US010252183B2

(12) United States Patent
Schultz et al.

(10) Patent No.: US 10,252,183 B2
(45) Date of Patent: *Apr. 9, 2019

(54) PRODUCT MANAGEMENT IN BIOLOGICAL CONVERSION PROCESSES

(71) Applicant: LanzaTech New Zealand Limited, Skokie, IL (US)

(72) Inventors: Michael Anthony Schultz, Skokie, IL (US); Thomas Ewald Raiser, Winterthur (CH); Rachel Jane Brenc, Skokie, IL (US)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 100 days.

This patent is subject to a terminal disclaimer.

(21) Appl. No.: 15/424,413

(22) Filed: Feb. 3, 2017

(65) Prior Publication Data

US 2017/0226538 A1    Aug. 10, 2017

Related U.S. Application Data

(60) Provisional application No. 62/291,508, filed on Feb. 4, 2016.

(51) Int. Cl.
*B01D 3/00* (2006.01)
*B01D 3/10* (2006.01)
(Continued)

(52) U.S. Cl.
CPC ............. *B01D 3/002* (2013.01); *B01D 3/007* (2013.01); *B01D 3/10* (2013.01); *B01D 3/141* (2013.01);
(Continued)

(58) Field of Classification Search
CPC .... C12P 7/06; C12P 7/54; C12P 7/065; C12P 7/6463; C12P 7/649; C12P 7/18; C12P 7/56; C12P 7/04; C12P 39/00; C12P 7/08; C12P 7/16; C12P 7/52; C12P 7/6427; C12P 7/6472; Y02E 50/13; Y02E 50/17; Y02E 50/16; Y02E 10/41; Y02E 10/45; Y02E 10/46; Y02E 10/47; Y02E 20/14; Y02E 20/16; Y02E 20/18; Y02E 50/10; Y02E 50/343; Y02E 60/142; Y02E 70/30; B01D 3/002; B01D 3/007; B01D 3/10; B01D 3/141; B01D 3/145; B01D 5/0039; B01D 5/0063; B01D 61/14; B01D 63/02; B01D 3/06; B01D 53/48; B01D 53/62; C12M 23/40; C12M 23/58; C12M 21/04; C12M 29/24; C12M 43/06; C12M 29/06; C12M 47/10; B01J 19/0093; B01J 19/24; B01J 2219/00864; B01J 2219/00867; B01J 2219/00871; B01J 2/00; B01J 6/008; B02C 23/00; B03C 1/00; B09B 5/00; B22F 2009/001; B22F 3/10; B22F 9/00; B29B 17/00; C01B 13/02; C01B 17/02; C01B 17/027; C01B 17/48; C01B 17/74; C01B 2203/0205; C01B 2203/0283; C01B 2203/043; C01B 2203/0445; C01B 2203/0475; C01B 32/05; C01B 32/20; C01B 32/50; C01B 3/32; C01G 21/02; C02F 1/00; C10G 11/18; C10G 1/00; C10G 1/02; C10G 1/10; C10G 31/08; C10G 33/00; C10G 45/00; C10G 57/00; C10G 75/04; C10G 7/00; C10G 7/003; C10G 7/06; C10J 2300/093; C10J 2300/0946; C10J 3/72; C10L 2290/544; C10L 9/10; C22B 13/00; C22B 15/00; C22B 21/00; C22B 7/00; C22B 9/00; F01K 13/00; F01K 13/02; F01K 25/00; F01K 3/00; F02G 1/043; F03G 6/067; F03G 6/068; F03G 7/04; F24S 2030/134; F24S 20/20;
(Continued)

(56) References Cited

U.S. PATENT DOCUMENTS 5,173,429 A    12/1992    Gaddy
5,593,886 A    1/1997    Gaddy
(Continued)

FOREIGN PATENT DOCUMENTS

EP    117309 A1    9/1984
WO    1998/00558    1/1998
(Continued)

OTHER PUBLICATIONS

Kaibel et al "Distallation columns with vertical partitions", Chemical Engineering & Technology / vol. 10, Issue 1, 1987, abstract only available (Can view online entire document if so desired at https://www.onlinelibrary.wiley.com).*
Abrini et al., *Clostridium autoethanogenum*, sp. no., an anaerobic bacterium that produces ethanol from carbon dioxide, Archives of Microbiology, 1994, pp. 345-351, 161.
Tanner et al., *Clostridium ljungdahlii* sp. nov., an Acetgenic Species in Clostridial rRNA Homology Group 1, International Journal of Systematic Bacteriology, Apr. 1993, pp. 232-236, 43.
(Continued)

*Primary Examiner* — Deborah K Ware
(74) *Attorney, Agent, or Firm* — James A Edwards (57) ABSTRACT

Improvements in biological conversion processes and associated apparatuses are disclosed for the generation of useful end products such as ethanol, through metabolic pathways of C1-fixing bacteria that utilize, as a nutrient, a C1-carbon source from a C1-containing substrate such as an industrial waste gas. Particular aspects of the disclosure relate to the downstream recovery of ethanol and/or isopropanol from bleed and permeate streams and more particularly to performing such recovery with improved efficiency that can advantageously reduce capital (e.g., equipment) and/or operating (e.g., utility) costs.

24 Claims, 2 Drawing Sheets

(51) Int. Cl.
*B01D 3/14* (2006.01)
*B01D 5/00* (2006.01)
*B01D 61/14* (2006.01)
*B01D 63/02* (2006.01)
*C12P 7/04* (2006.01)
*C12P 7/06* (2006.01)

(52) U.S. Cl.
CPC ........... *B01D 3/145* (2013.01); *B01D 5/0039* (2013.01); *B01D 5/0063* (2013.01); *C12P 7/04* (2013.01); *C12P 7/06* (2013.01); *C12P 7/065* (2013.01); *B01D 61/14* (2013.01); *B01D 63/02* (2013.01)

(58) Field of Classification Search
CPC .. F24S 23/74; F24S 23/79; F24S 25/50; F24S 30/425; F24S 40/20; F27B 17/00; F28D 20/0039; G01N 33/92; H01M 10/54; H01M 8/00; H02K 55/02; H02K 7/09; Y02P 10/143; Y02P 20/129; Y02P 30/446; Y02P 80/24; Y02W 10/33; Y02W 10/37; Y02W 30/84; C12R 1/145
See application file for complete search history.

(56) References Cited

U.S. PATENT DOCUMENTS 6,368,819 B1 4/2002 Gaddy
10,010,807 B2 * 7/2018 Schultz .................. B01D 3/002
2011/0212433 A1 9/2011 Barker et al.

FOREIGN PATENT DOCUMENTS

| WO | 2000/68407 | 11/2000 |
| WO | 2002/008438 A2 | 1/2002 |
| WO | 2007/117157 A1 | 10/2007 |
| WO | 2008/028055 A2 | 3/2008 |
| WO | 2008/115080 A1 | 9/2008 |
| WO | 2009/022925 A1 | 2/2009 |
| WO | 2010/093262 A1 | 8/2010 |
| WO | 2011/002318 A1 | 1/2011 |

OTHER PUBLICATIONS

Perez et al., Biocatalytic reduction of Short-Chain Carboxylic Acids into their Corresponding Alcohols with Syngas Fermentation, Biotechnology Bioengineering, 2012, pp. 1066-1077, 110.

Köpke et al., Fermentative production of ethanol from carbon monoxide, Current Opinion in Biotechnology, 2011, pp. 320-325, 22.

Tirado-Acevedo et al., Production of bioethanol from synthesis gas using *Clostridium ljungdahlii*, PhD thesis, North Carolina State University, 2010.

* cited by examiner

PRODUCT MANAGEMENT IN BIOLOGICAL CONVERSION PROCESSES

FIELD OF THE INVENTION

Aspects of the invention relate to the microbial fermentation of a C1-containing substrate to ethanol, utilizing a bioreactor system that produces a filtered permeate stream and bacteria-containing bleed stream. Aspects more specifically relate to processes for obtaining ethanol from these streams in an efficient manner, particularly in terms of heat integration.

DESCRIPTION OF RELATED ART

Environmental concerns over fossil fuel greenhouse gas (GHG) emissions have led to an increasing emphasis on renewable energy sources. As a result, ethanol is rapidly becoming a major hydrogen-rich liquid transport fuel around the world. Continued growth in the global market for the fuel ethanol industry is expected for the foreseeable future, based on increased emphasis on ethanol production in Europe, Japan, and the United States, as well as several developing nations. For example, in the United States, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. In addition, the European Union (EU) has mandated targets, for each of its member nations, for the consumption of sustainable transport fuels such as biomass-derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value in the marketplace for competing uses, namely as food sources for both humans and animals. In addition, the cultivation of starch or sucrose-producing crops for ethanol production is not economically sustainable in all geographies, as this is a function of both local land values and climate. For these reasons, it is of particular interest to develop technologies to convert lower cost and/or more abundant carbon resources into fuel ethanol. In this regard, carbon monoxide (CO) is a major, energy-rich by-product of the incomplete combustion of organic materials such as coal, oil, and oil-derived products. CO-rich waste gases result from a variety of industrial processes. For example, the steel industry in Australia is reported to produce and release into the atmosphere over 500,000 metric tons of CO annually.

More recently, micro-organism (bacterial) based process alternatives for producing ethanol from CO on an industrial scale have become a subject of commercial interest and investment. The ability of micro-organism cultures to grow, with CO being the sole carbon source, was first discovered in 1903. This characteristic was later determined to reside in an organism's use of the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic, and acetogenic organisms have since been shown to metabolize CO. Anaerobic bacteria, such as those from the genus *Clostridium*, are known to produce ethanol from CO, $CO_2$ and $H_2$ via the acetyl CoA biochemical pathway. For example, various strains of *Clostridium ljungdahlii* that produce ethanol from gases are described in WO 00/68407; EP 1117309 A1; U.S. Pat. No. 5,173,429; U.S. Pat. No. 5,593,886; U.S. Pat. No. 6,368,819; WO 98/00558; and WO 02/08438. The bacterium *Clostridium autoethanogenum* sp is also known to produce ethanol from gases (Abrini et al., ARCHIVES OF MICROBIOLOGY 161: 345-351 (1994)).

Because each enzyme of an organism promotes its designated biological conversion with essentially perfect selectivity, microbial synthesis routes can achieve higher yields with lower energy costs compared to conventional catalytic routes. In addition, concerns over the poisoning of catalysts, due to impurities in the reaction medium, are diminished. Despite these apparent advantages associated with the microbial synthesis of ethanol from CO, such processes must nonetheless be competitive with other technologies, in terms of ensuring that the production rate is competitive. When using CO as their carbon source, the anaerobic bacteria described above produce ethanol by fermentation, but they also produce at least one metabolite, for example $CO_2$, methane, n-butanol, and/or acetic acid. The formation of any of these metabolites has the potential to significantly impact productivity and overall economic viability of a given process, as available carbon is lost to the metabolite(s) and the production efficiency of the desired end product is compromised. In addition, unless a metabolite (e.g., acetic acid) itself has value at the time and place of the microbial fermentation process, it may pose a waste disposal problem. Various proposals for addressing the formation of products other than the desired end product in the anaerobic fermentation of CO-containing gases to make ethanol are discussed in WO2007/117157, WO2008/115080 and WO2009/022925.

Ethanol production rate, which is a key determinant as to whether a given fermentation process is economically attractive, is highly dependent on managing the appropriate conditions for bacterial growth. For example, it is known from WO2010/093262 that the CO-containing substrate must be provided to a microbial culture at a rate that results in optimal microbial growth and/or desired metabolite production. If insufficient substrate is provided, microbial growth slows and the fermentation product yields shift toward acetic acid at the expense of ethanol. If excessive substrate is provided, poor microbial growth and/or cell death can result. Further information regarding the relationships among operating parameters in these processes is found in WO2011/002318.

The art of biological processes for producing ethanol from CO, and particularly CO-containing waste streams such as the gaseous effluents emitted in steel production, is continually seeking solutions that improve process economics and therefore industry competitiveness. One area of interest relates to the energy requirements for separating byproducts, namely the metabolites described above that result from non-selective side reactions, as well as components of the bacterial culture medium (especially water), from the desired ethanol product. For example, achieving even modest advances in heat integration associated with the required separations downstream of the bioreactor(s), particularly if capital and operating expenses are not substantially impacted, can have significant implications on the industrial scale of operation.

SUMMARY OF THE INVENTION

Aspects of the invention relate to improvements in biological conversion processes and associated apparatus for the generation of useful end products, through metabolic pathways of bacterium that utilize, as a nutrient, carbon from a carbon containing substrate. Representative processes comprise feeding a substrate to a bioreactor system comprising at least a first bioreactor including a culture medium and a bacterium to metabolize a carbon source in the substrate and produce at least one fermentation product; withdrawing from the bioreactor system a permeate stream obtained from filtration of a liquid product of the bioreactor system; withdrawing from the bioreactor system a bleed stream comprising bacterium; feeding at least a portion of the permeate stream to a high pressure separator; and feeding at least a portion of the bleed stream to a low pressure separator. In particular embodiments, the process further comprises combining a second portion of the permeate stream with the bleed stream to provide a combined stream, and feeding the combined stream to the low pressure separator. In other embodiments, the process comprises partitioning the permeate stream into at least a first permeate portion and a second permeate portion and feeding the first permeate portion to a high pressure separator and feeding the second permeate portion to a low pressure separator.

According to further aspects, the invention relates to improvements in biological conversion processes and associated apparatuses for the generation of useful end products such as ethanol and/or isopropanol, through metabolic pathways of C1-fixing bacteria that utilize, as a nutrient, C1 gases from a C1 containing substrate such as an industrial waste gas. Representative processes and apparatuses involve alternative types of operation that are particularly advantageous in conjunction with high ethanol or isopropanol productivities. The associated, substantial product flow rates must be processed in an efficient manner through the separation unit operations needed to achieve a high purity end product (e.g., anhydrous ethanol or isopropanol). An exemplary bioreactor system that may be used for achieving desirable ethanol or isopropanol productivity (e.g., expressed in terms of grams per day per liter of bioreactor volume) may comprise two or more bioreactors operating in series with respect to the flow of liquid inputs and outputs.

That is, according to such a system, a feed stream of liquid culture medium may be passed to a first bioreactor, and one or more liquids comprising contents of this bioreactor (having the same or different compositions relative to the bulk, first bioreactor liquid) may be passed to a second bioreactor, with one or more liquids comprising contents of the second bioreactor (having the same or different compositions relative to the bulk, second bioreactor liquid) being processed through separation unit operations to purify the ethanol or isopropanol contained in these liquids. This advantageously allows for the separate control of conditions in separate bioreactors for differing objectives (e.g., bacterial growth vs. product yield), leading to enhancements in ethanol productivity and/or reductions in byproduct productivity, relative to the use of a single reactor with comparable overall volume. If a bioreactor system includes more than two bioreactors, then intermediate liquid products may be fed to, and withdrawn from, intermediate bioreactors in series (i.e., passed to successively downstream bioreactors). The terms "subsequent" or "downstream," when referring to a bioreactor, refer to its position with respect to other bioreactors of a bioreactor system, in terms of the passage of reactor liquids (e.g., culture medium) from one bioreactor to the next. Representative bioreactor systems comprising two or more bioreactors may also operate in parallel with respect to the flow of gaseous feeds and products, such that a gaseous C1-containing substrate may be divided and fed at the same or differing flow rates to the bioreactors simultaneously (e.g., by introducing the substrate to gas distributors in their lower sections). Gaseous products, depleted in C1 gas composition relative to the substrate, may be withdrawn separately from each of the bioreactors simultaneously and then further processed, for example to recover entrained liquid product, as separate streams or as a combined stream.

Whilst the description that follows pertains to ethanol fermentations, it is considered that the teachings are equally applicable to isopropanol fermentation processes and isopropanol purification processes. Furthermore, whilst the embodiments provided relate to gas fermentation processes, it is considered that the invention would be applicable to any fermentation process generating a fermentation broth containing excreted liquid products and biomass, During normal operation of a bioreactor system, the net generation of liquid products requires that these products be withdrawn, preferably on a continuous basis, to prevent their accumulation in each bioreactor and thereby maintain steady-state conditions. If all of the withdrawn liquid has the same, bulk composition as that existing in the bioreactor (including the same concentrations of bacteria and culture medium components), then the bioreactor, although operating at steady-state with respect to ethanol and acetic acid concentration, would become steadily depleted in bacteria concentration. Under such circumstances, a greater productivity of ethanol relative to the productivity (growth) of bacteria would result directionally in a faster rate of bacteria depletion from a given bioreactor. In order to maintain bacteria concentration by providing an additional operating degree of freedom, a first part of the liquid withdrawn from a given bioreactor, i.e., a bleed stream, may be an unfiltered part, whereas a second part of the liquid withdrawn may be filtered. In this case, the first part may have substantially the same, bulk composition as that existing in the bioreactor, or at least substantially the same bacteria concentration, whereas the second part of the liquid, by virtue of filtration, may be divided into a filtration retentate that is enriched in bacteria and returned to bioreactor to maintain its bacteria concentration, and a filtration permeate that represents the net fraction of the withdrawn, second part that is actually removed from the bioreactor (or not recycled to the bioreactor). This filtration permeate, substantially free of bacteria, may then be passed to a downstream bioreactor, or, in the case of its removal from the final bioreactor, may be processed through separation unit operations to purify the ethanol contained therein.

In this manner, the withdrawal of both bleed and permeate streams provides for a significantly improved degree of overall process control, especially in terms of managing the bacteria concentration in a bioreactor at varying levels of productivity. As the rate of ethanol generation increases, the flow of the permeate stream relative to the flow of the bleed stream can be increased, allowing more filtered reactor liquid to be withdrawn with greater retention of bacteria. Because ethanol is present in both of these withdrawn streams, the bleed and permeate streams that are ultimately withdrawn from a bioreactor system, for example from a final stage bioreactor (such as from a second bioreactor of a bioreactor system comprising first and second bioreactors operating in series with respect to liquid flow), are normally both further processed for ethanol purification. The bleed and permeate streams are sent to individual storage tanks, with effluents from these tanks then sent to downstream recovery units.

In view of this, aspects of the present invention relate to the downstream recovery of ethanol or isopropanol from bleed and permeate streams and more particularly to performing such recovery with improved efficiency that can advantageously reduce capital (e.g., equipment) and/or operating (e.g., utility) costs. More specific aspects relate to processes and associated apparatuses for the purification of ethanol or isopropanol contained in both bleed and permeate streams, withdrawn from bioreactor processes, based on differences in relative volatility between ethanol (normal boiling point=78° C.) and other components in these streams, including water (normal boiling point=100° C.), as well as metabolites such as acetic acid (normal boiling point=118° C.), 2,3-butanediol (normal boiling point=177° C.), and various other simple organic alcohols and acids. Exemplary processes and apparatuses utilize at least a single stage of vapor-liquid equilibrium to achieve the desired enrichment of ethanol or isopropanol in a vapor or overhead fraction of a separator, which separates this fraction from a liquid or bottoms fraction. The term "separator" therefore encompasses a single-stage flash drum. Preferably, however, a representative separator will utilize multiple stages of vapor-liquid equilibrium, as in the case of a distillation column, in order to achieve higher purity of the ethanol or isopropanol product in the overhead. The term "separator" also encompasses such single-stage or multi-stage vessels having an auxiliary flow of gas (e.g., a stripper) and/or an auxiliary flow or liquid (e.g., a scrubber) to enhance a desired component separation.

Regardless of the type of separator, however, an input of heat is usually necessary to carry out such separation processes, and, more particularly, a consumption of heat at a relatively high temperature in at least one stage, such as a reboiler stage, which may be accompanied by a recovery of heat at a relatively low temperature in another stage, such as a condenser stage. In this regard, further aspects of the present invention more particularly relate to the discovery of processes and apparatuses with which heat integration is improved in the recovery of ethanol or isopropanol from bleed and permeate streams that are withdrawn from bioreactor systems. Such recovery is complicated by the fact that the former stream contains some of the bacteria used in the biological conversion process, whereas the latter stream is normally free or at least substantially free of such bacteria. The presence of bacteria in the bleed stream, for example, places constraints on the operating temperatures used in a distillation column or other separator used to purify this stream, while the same considerations do not apply in processing the permeate stream.

This understanding has led to the solution of processing the bleed stream in a separator operating at lower temperature, and consequently lower pressure, relative to that of a separator for processing the permeate stream. As noted above, however, higher productivity directionally results in a greater flow rate of the permeate stream relative to the flow rate of the bleed stream. A significant offset in flow rates, in turn, causes a proportionate offset in heat input (duty) to the separators, as required to process (e.g., distill) the bleed and permeate streams. Moreover, an offset in operating temperature, between (i) a high pressure separator used for separation of products such as ethanol or isopropanol from the permeate stream, or at least from a first portion thereof, and (ii) a low pressure separator used for separation of ethanol or isopropanol from the bleed stream, optionally in conjunction with separation of ethanol or isopropanol from a second portion of the permeate stream as described herein, allows for heat integration between the high pressure separator and low pressure separator, or more particularly, heat transfer from the high pressure separator to the low pressure separator. Heat integration may be achieved by recovering, at a relatively high temperature, heat from any material stream associated with the high pressure separator, for consumption, at a relatively low temperature, by any material stream associated with the low pressure separator. In the case of distillation columns or other types of separators, heat may be consumed in, or input to, a reboiler that is used to heat, and optionally at least partially vaporize, a bottoms liquid product, for example a reflux portion of the low pressure separator bleed liquid or the low pressure separator permeate liquid. Heat may be recovered, or withdrawn from, a condenser that is used to cool, and optionally at least partially condense, an overhead vapor product, for example a reflux portion of the high pressure separator overhead. According to one embodiment, therefore, heat may be transferred from the high pressure separator condenser (e.g., with the high pressure separator vapor outlet stream passing therethrough at a relatively high temperature, albeit at substantially the lowest temperature of the high pressure separator, such as the high pressure distillation column) to a reboiler of the low pressure separator (e.g., with the low pressure separator bleed liquid outlet stream and/or the low pressure separator permeate liquid outlet stream passing therethrough at a relatively low temperature, albeit at substantially the highest temperature of the low pressure separator, such as the low pressure distillation column).

According to further aspects of the present invention, an opportunity to improve heat integration in the face of differing bleed stream and permeate stream flow rates arises in processing at least part, and optionally all, of the permeate stream together with the bleed stream in a single separator. In this regard, aspects of the invention exploit the particular characteristics of the bleed and permeate streams in the recovery of ethanol or isopropanol, namely their differing compositions in terms of non-volatile components (and particularly the bacteria concentration) but similar, or identical, compositions in terms of proportions of volatile components (and particularly ethanol or isopropanol, water, and acetic acid concentrations on a bacteria-free basis). Such characteristics are used as a basis for obtaining efficient heat integration and other advantages, including reduced equipment capacity and/or cost, according to processes and associated apparatuses described herein.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which the same or similar features are identified by the same or similar reference numbers.

FIGS. 1 and 2 should be understood to present an illustration of the disclosure and/or principles involved. In order to facilitate explanation and understanding, simplified process flow schemes and equipment are depicted, and these figures are not necessarily drawn to scale. Details including valves, instrumentation, and other equipment not essential to the understanding of the disclosure are not shown. The Figures are directed to processes for ethanol production and recovery, however, it is considered that the disclosure and principles involved are equally applicable to isopropanol production. As is readily apparent to one of skill in the art having knowledge of the present disclosure, processes for recovering ethanol from streams produced in bioreactor systems in an equipment cost-efficient manner and/or a utility cost-efficient manner, according to other embodiments of the invention, will have configurations determined, in part, by their specific use.

DETAILED DESCRIPTION

Exemplary embodiments of the invention are directed to biological conversion process comprising feeding a substrate to a bioreactor system comprising at least a first bioreactor including a culture medium and a bacterium to metabolize a carbon source in the substrate and produce at least one fermentation product. The process further comprises withdrawing from the bioreactor system a permeate stream obtained from filtration of a liquid product of the bioreactor system, and partitioning the permeate stream into at least a first permeate portion and a second permeate portion and feeding the first permeate portion to a high pressure separator (e.g. high pressure distillation column) and feeding the second permeate portion to a low pressure separator (e.g. low pressure distillation column).

Particular embodiments of the invention are directed to biological conversion processes comprising feeding a gaseous C1-containing substrate to a bioreactor system comprising at least (i) a first bioreactor including a culture medium and C1-fixing bacteria (cells or biomass), which may be contained the first bioreactor, and optionally (ii) a second or additional downstream bioreactors, with the bioreactors being utilized to metabolize a C1 component in the C1-containing substrate and thereby produce ethanol. The processes further comprises withdrawing from the bioreactor system a bleed stream comprising C1-fixing bacteria, and also withdrawing from the bioreactor system a permeate stream obtained from filtration of a liquid product of the bioreactor system. In particular embodiments the process further comprises partitioning the permeate stream into at least a first permeate portion and a second permeate portion and feeding the first permeate portion to a high pressure separator (e.g., stripper or distillation column) and feeding the second permeate portion to a low pressure separator (e.g., stripper or distillation column). The bleed stream comprises at least a portion of the C1-fixing bacteria originally in the first bioreactor of the bioreactor system and passed to subsequent or downstream bioreactors. A bleed stream may more generally include any liquid product removed from a bioreactor of the system, which has not been filtered or at least not completely filtered. In certain embodiments at least a portion of the bleed stream is fed to the low pressure separator. In certain embodiments, at least a portion of the bleed stream and at least a portion of the second permeate portion are blended to provide a combined stream, and the combined stream is fed to the low pressure separator. Representative processes may further comprise feeding at least a portion of the bleed stream to the low pressure separator and withdrawing a low pressure separator overhead enriched in ethanol, relative to one or more feed streams to the low pressure separator, e.g., both the second permeate portion and the bleed stream. The low pressure separator overhead may additionally be depleted, relative to these streams, in one or more components present in these streams that are less volatile than ethanol, such as water, acetic acid, and 2,3-butanediol.

In embodiments involving the use of both a high pressure separator (e.g., high pressure distillation column) for purifying ethanol from a first permeate portion and a low pressure separator (e.g., low pressure distillation column) for purifying ethanol from a second permeate portion, in conjunction with purifying ethanol from at least a portion of the bleed stream, heat integration may include utilizing heat generated in one of the separators for consumption in the other separator. Advantageously, a condenser temperature of the high pressure separator may exceed a reboiler temperature of the low pressure separator, such that at least a portion of the high pressure separator condenser heat may be consumed as reboiler heat in the low pressure separator reboiler (e.g., a low pressure separator reboiler used to vaporize at least a portion of a low pressure separator liquid outlet stream).

Yet other embodiments of the invention are directed to biological conversion apparatuses comprising a bioreactor system comprising (i) an inlet (e.g., in fluid communication with at least one, at least two, and/or all bioreactors of the bioreactor system) for introducing a substrate to the bioreactor system, (ii) at least a first bioreactor for containing a culture medium and bacteria to metabolize a carbon component in the substrate and produce a desired end product, (iii) a filtration system for filtering a liquid product of the bioreactor system, (iv) a bleed stream outlet (e.g., in fluid communication with at least one bioreactor of the bioreactor system) for withdrawing a bleed stream comprising bacteria, and (v) a permeate stream outlet in fluid communication with a permeate side of the filtration system for withdrawing a permeate stream from the bioreactor system. The apparatuses may optionally comprise a recycle conduit in fluid communication with a retentate side of the filtration system for maintaining a recycle portion of bacteria in the bioreactor system. In particular aspects, the biological conversion apparatus comprises a bioreactor system comprising (i) an inlet for introducing a C1-containing substrate, to the bioreactor system, (ii) at least a first bioreactor for containing a culture medium and C1-fixing bacteria to metabolize a C1 component in the C1-containing substrate and produce at least one product selected from the group consisting of ethanol, isopropanol and mixtures thereof.

Representative apparatuses further comprise a low pressure separator having (i) a low pressure separator stream inlet and (ii) a low pressure separator liquid outlet positioned below the low pressure stream inlet. According to certain embodiments, the low pressure separator may be configured with a low pressure separator condenser in fluid communication with the low pressure separator vapor outlet and both (i) a low pressure separator overhead reflux conduit and (ii) a low pressure separator overhead conduit. The low pressure separator may also be configured with a low pressure separator reboiler in fluid communication with the low pressure separator liquid outlet and both (i) a low pressure separator liquid reflux conduit and (ii) a low pressure separator bottoms conduit.

Representative apparatuses may optionally further comprise a high pressure separator having (i) a first permeate portion inlet in fluid communication with the permeate stream outlet, for receiving a first permeate portion of the permeate stream and passing a second permeate portion of the permeate stream to the low pressure separator permeate stream inlet, (ii) a high pressure separator vapor outlet (for example, in the upper section, such as at or near the top of the high pressure separator), and (iii) a high pressure separator liquid outlet (for example, in the lower section, such as at or near the bottom). The first permeate portion inlet is normally positioned below the high pressure separator overhead outlet and above the high pressure separator bottoms outlet. The high pressure separator may be configured with a high pressure separator condenser in fluid communication with the high pressure separator vapor outlet and both (i) a high pressure separator overhead reflux conduit and (ii) a high pressure separator overhead conduit. The high pressure separator may also be configured with a high pressure separator reboiler in fluid communication with the high pressure separator liquid outlet and both (i) a high pressure separator liquid reflux conduit and (ii) a high pressure separator bottoms conduit. Any of, or any combination of, the low pressure separator condenser and the low pressure separator reboiler, as described above, may be configured to provide heat integration with the high pressure separator condenser and/or the high pressure separator reboiler, as described above. According to exemplary embodiments, the high pressure separator condenser may be configured to transfer heat generated in this condenser, to be consumed in the low pressure separator reboiler as described above.

Representative apparatuses may optionally also comprise a dehydration column having (i) a dehydration column inlet in fluid communication with both the low pressure separator overhead outlet and the high pressure separator overhead outlet, (ii) a dehydration column overhead outlet (for example, in the upper section, such as at or near the top), and (iii) a dehydration column bottoms outlet (for example, in the lower section, such as at or near the bottom). The dehydration column inlet is normally positioned below the dehydration column overhead outlet and above the dehydration column bottoms outlet. Representative apparatuses may optionally additionally comprise a second filtration system in fluid communication with the low pressure separator bleed bottoms outlet, for filtering a low pressure separator bleed bottoms stream, for example to separate C1-fixing bacteria contained in this stream.

In view of the above, particular aspects of the invention are directed to biological conversion processes and associated apparatuses, in which a C1-containing substrate is fed to a bioreactor system comprising at least one bioreactor, for the production of a fermentation product that is recovered from the bioreactor system in liquid permeate and bleed streams. In particular aspects, the fermentation product is selected from the group consisting of ethanol ($C_2H_5OH$) and isopropanol ($C_3H_7OH$). Bioreactor systems comprising multiple (e.g., two or more, such as two, three, or four) bioreactors can advantageously allow for the separate control of conditions in each bioreactor to accomplish different processing objectives. For example, in the case of a bioreactor system comprising two bioreactors, a first bioreactor may be operated primarily for growth of the bacterial culture that is supplied continuously or intermittently to a second bioreactor. The second bioreactor, in turn, may be operated primarily for the generation of ethanol, i.e., the maximization of ethanol or isopropanol product yield.

The use of such bioreactor systems, with a parallel flow of the C1-containing substrate to the bioreactors and series flow of liquid products from a first bioreactor to subsequent bioreactor(s), as described above, is associated with high fermentation product concentrations in liquid bleed stream(s) and liquid permeate stream(s) that are withdrawn from the bioreactor system, as described herein. Often, all or substantially all of the ethanol produced in a biological conversion process is recovered from bleed and permeate streams withdrawn from a final bioreactor, which is namely the most downstream bioreactor of the bioreactor system (e.g., in the case of the final bioreactor being a second bioreactor, positioned downstream of a first bioreactor, in a bioreactor system having two and only two bioreactors). It is also possible, however, for at least a portion of the ethanol produced to be recovered from a bleed stream and/or a permeate stream withdrawn from the first bioreactor and/or any intermediate bioreactors (upstream of the final bioreactor) of a bioreactor system. In representative embodiments, the C1 containing substrate is a gaseous substrate comprising CO. In representative embodiments, any such bleed and/or permeate stream(s), for example withdrawn from a final bioreactor, may have an ethanol concentration of generally at least about 40 grams per liter (grams/liter or g/L) (e.g., from about 40 to about 95 g/L), typically at least about 50 g/L (e.g., from about 50 to about 80 g/L), and often at least about 60 g/L (e.g., from about 60 to about 75 g/L). Any such bleed and/or permeate stream(s), for example withdrawn from a final bioreactor, may have a weight ratio of ethanol to acetic acid of generally at least about 5:1 (e.g., from about 5:1 to about 100:1), typically at least about 7.5:1 (e.g., from about 7.5:1 to about 50:1), and often at least about 10:1 (e.g., from about 10:1 to about 50:1). In general, the analytical methods (e.g., gas chromatography (GC) or high pressure liquid chromatography, HPLC) used to determine concentrations of ethanol and other metabolites require cell-free samples, and therefore may require an initial separation (e.g., membrane filtration) to be performed on the bleed stream to remove C1-fixing bacteria (cells or biomass). Accordingly, concentrations of ethanol and other metabolites, as well as other properties of bleed streams as described herein (e.g., the ethanol:acetic acid weight ratio) are expressed on a biomass-free basis.

The present invention therefore generally relates to processes for producing a desired end product, such as ethanol or isopropanol, by feeding C1-carbon source in a gaseous C1-containing substrate to a bioreactor system comprising one or more bioreactors. In operation, the one or more bioreactors comprise a liquid culture medium containing C1-fixing bacteria. In addition to the desired end product, processes as described herein additionally generate undesired or less desired metabolites. Examples of metabolites that may be generated in addition to a desired fermentation product, are acetate (e.g., in the form of acetic acid), 2,3-butanediol, and lactate (e.g., in the form of lactic acid). Gaseous $CO_2$ may also be generated.

Representative bacteria or microbes of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/− [1] | − | − | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/− [2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | − [3] | + | + | − |
| *Oxobacter pfennigii* | + | + | + | − | + | + | − |
| *Sporomusa ovata* | + | + | + | − | + | +/− [4] | − |
| *Sporomusa silvacetica* | + | + | + | − | + | +/− [5] | − |
| *Sporomusa sphaeroides* | + | + | + | − | + | +/− [6] | − |
| *Thermoanaerobacter kiuvi* | + | + | + | − | + | − | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of CO or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 5-70, 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired contaminants, such as toxins (for example, HCN, acetylene), undesired components, or dust particles, and/or increase the concentration of desirable components. For example, the gaseous C1-containing substrate may be filtered (contacted with a solid medium, such as activated carbon) or scrubbed (contacted with a liquid medium, such as an aqueous solution of an acid, a base, an oxidizing agent, or a reducing agent) using known methods, or otherwise may be subjected to adsorption to remove preferentially adsorbed contaminants. Pressure swing adsorption (PSA) and/or temperature swing adsorption (TSA), in particular, may be used to remove contaminants that are detrimental to the functioning of the carboxydotrophic bacteria, such as hydrogen cyanide (HCN) and aromatic compounds including benzene, toluene, and/or xylenes (BTX). The substrate preferably does not include contaminants, to the extent that such contaminants might have an adverse effect on the growth of the carboxydotrophic bacteria (e.g., one or more contaminant(s) are not present in concentrations or amounts such that the growth rate is reduced by more than 10% under a given set of conditions, compared to the growth rate under the same conditions, but without the contaminant(s)

Whilst representative embodiments of the invention disclose the use of C1-carbon sources, and C1-fixing bacterium, it is considered that aspects of the invention apply to any biological conversion process whereby both a permeate stream and a bleed stream are withdrawn from a bioreactor.

Broader aspects of the invention are intended to capture non-gaseous fermentation processes, as well as microorganisms and feedstocks applicable to the fermentation process.

In particular aspects, the non-gaseous substrate is a carbohydrate substrate, and the bacterium is a bacterium capable of fixing a carbon substrate in the carbohydrate substrate. Processes for the conversion of carbohydrate substrates to products, including ethanol, are known. Carbohydrate feedstocks may include sugars (for example glucose, sucrose, fructose, xylose, arabinose and glycerol) cellulose, and biomass (for example, corn starch, sugarcane, crop residues such as corn stover and sugarcane bagasse, purpose-grown grass crops, and woody plant biomass.

In particular aspects, the microorganism applicable to the fermentation process is selected from the group consisting of yeast, fungus, algae, cyanobacteria or bacteria. Exemplary bacterium, applicable to the fermentation process, include *Escherichia coli, Klebsiella oxytoca, Bacillus subtilus, Zymomonas mobilis, Lacotococcus lactis,* and *Clostridium acetobutylicum.* Exemplary yeasts of fungi include species from the genus *Saccharomyces, Candida, Lipomyces, Rhodosporidium, Rhodotorula,* and *Yarrowia.*

In the context of an acidic metabolite that is acetic acid, the terms "acetic acid" or "acetate" refer to the total acetate present in the culture medium, either in its anionic (dissociated) form (i.e., as acetate ion or $CH_3COO_-$) or in the form of free, molecular acetic acid ($CH_3COOH$), with the ratio these forms being dependent upon the pH of the system. The terms "lactic acid" and "lactate" are used analogously, to refer to the total lactate present in the culture medium. As described below, a basic neutralizing agent such as aqueous sodium hydroxide (NaOH) may be used to control the pH of the culture medium in a given bioreactor (e.g., to a pH value that may be between pH=4.0 and pH=8.0), for example by neutralizing acetic acid and optionally other minor acidic components. Representative pH ranges at which bioreactors are maintained for carrying out the processes described herein are from about 4.5 to about 7.0, such as from about 4.5 to about 6.5.

A specific type of bioreactor that is particularly useful in the practice of the present invention is a circulated loop reactor that relies on a density gradient between a relatively low density section within a riser and a relatively high density section within one or more, internal or external downcomers. Both the riser and downcomer sections include liquid culture medium in a continuous liquid phase zone, but the gaseous C1-containing substrate is normally distributed (e.g., sparged) into the bottom of the riser section only. Rising gas bubbles are confined to this section during their upward movement through the continuous liquid phase zone, until any unconsumed and undissolved gas is released into a continuous gas phase zone (i.e., vapor space or headspace) above the liquid level. The downward liquid circulation, through either an internal or external liquid downcomer, may be induced or aided by an optional loop pump.

The term "bioreactor," as well as any bioreactor that may be included as part of a "bioreactor system," is not limited to a circulated loop reactor, but more broadly includes any suitable vessel, or section within a vessel, for maintaining a liquid volume of culture medium with C1-fixing bacteria that may be used to carry out the biological processes described herein, which may also be referred to as fermentation processes to the extent that they are generally conducted anaerobically. Particular types of bioreactors can include any vessels suitable for two-phase (gas-liquid) contacting, for example counter-current flow reactors (e.g., with an upwardly-flowing vapor phase and downwardly-flowing liquid phase) or co-current flow reactors (e.g., with upwardly-flowing gas and liquid phases). In such two-phase contacting vessels, it is possible for the liquid phase to be the continuous phase, as in the case of gas bubbles flowing through a moving column of liquid. Otherwise, it is possible for the vapor phase to be the continuous phase, as in the case of a dispersed liquid (e.g., in the form of droplets) flowing through a vapor space. In some embodiments, different zones of a bioreactor may be used to contain a continuous liquid phase and a continuous gas phase.

Specific examples of bioreactors include Continuous Stirred Tank Reactors (CSTRs), Immobilized Cell Reactors (ICRs), Trickle Bed Reactors (TBRs), Moving Bed Biofilm Reactor (MBBRs), Bubble Columns, Gas Lift Fermenters, and Membrane Reactors such as Hollow Fiber Membrane Bioreactors (HFMBRs). Suitable bioreactors may include static mixers, or other vessels and/or devices (e.g., towers or piping arrangements), suitable for contacting the gaseous C1-containing substrate with a culture medium and particularly the C-fixing bacteria contained therein (e.g., with dissolution and mass transport kinetics favorable for carrying out the biological conversion process). A bioreactor system may comprise two or more bioreactors of different types, although generally all bioreactors in a bioreactor system are of one type (e.g., circulated loop reactors).

Some suitable process streams, operating parameters, and equipment for use in the biological processes described herein are described in U.S. patent application Publication No. US2011/0212433, which is hereby incorporated by reference in its entirety. One or more bioreactors, for example all bioreactors, of bioreactor systems described herein may have a superatmospheric pressure, for example generally in the range from about 50 kPag (in which the notation "kPag" is meant to indicate units of kPa gauge pressure) to about 1,000 kPag and often in the range from about 200 kPa to about 800 kPag. One or more bioreactors, and preferably all bioreactors, of bioreactor systems described herein have a fermentation broth temperature that is suitable for vitality and growth of the C1-fixing bacteria. Representative temperatures are in a range from about 25° C. to about 45° C., and more typically from about 30° C. to about 40° C.

Bioreactor systems with multiple bioreactors operating in series with respect to the flow of liquid inputs and outputs and also operating in parallel with respect to the flow of gaseous feeds and products, as described herein, can provide favorable overall C1 utilization. The overall C1 utilization refers to the percentage of C1 that is input to the bioreactor system (e.g., the total C1-carbon source in the C1-containing substrate that is fed to the bioreactors) and utilized in the conversion to fermentation products(s) (e.g., ethanol or isopropanol) and other metabolites of the bacteria. If the combined composition of the gaseous product withdrawn from the bioreactor system (i.e., the combined gas outlet stream(s) withdrawn from the bioreactor(s)) is known or can be calculated (e.g., based on the flow rates and compositions of the gas outlet stream(s)), then the overall CO utilization may be calculated as:

1−(rate of CO withdrawn from the system)/(rate of CO fed to the system).

The overall CO utilization is determined on a "per pass" or "once-through" basis, without accounting for the use of gaseous product recycle (and added expense) that can provide higher total utilization values. According to representative embodiments, the CO utilization by the C1-fixing bacteria is generally at least about 35% (e.g., from about 35% to about 85%), typically at least about 50% (e.g., from about 50% to about 80%), and often at least about 60% (e.g., from about 60% to about 75%). In some cases, CO utilization may be at least about 70%.

Figure 1:
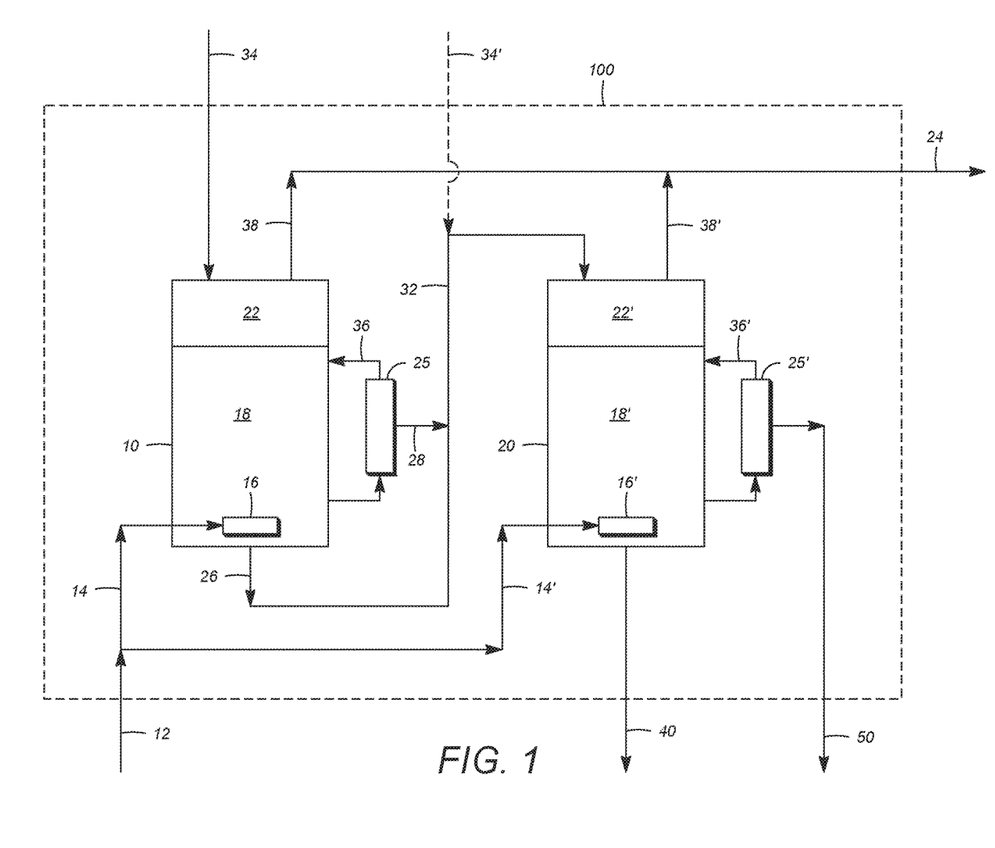
FIG. 1 depicts a representative bioreactor system utilizing two bioreactors, which provide a bleed stream and a permeate stream as described herein.

FIG. 1 depicts a representative bioreactor system 100 comprising a first bioreactor 10 and a second bioreactor 20. As shown, CO-containing substrate 12 to bioreactor system 100 is divided into separate, first bioreactor gas inlet stream 14 and second bioreactor gas inlet stream 14', which are fed, respectively, to first and second bioreactors 10, 20 through their respective gas inlets 16, 16', positioned near the bottoms of bioreactors 10, 20. Gas inlet streams 14, 14' may be fed through respective gas distributors, such as spargers, positioned at gas inlets 16, 16' and configured to produce fine bubbles (not shown) of CO-containing substrate in respective continuous liquid phase zones 18, 18' of bioreactors 10, 20 and thereby improve gas-liquid mass transfer.

As described above, the bacteria concentration in continuous liquid phase zones 18, 18' of bioreactors 10, 20 can be maintained at varying levels of ethanol productivity (corresponding to varying liquid product withdrawal rates) by providing a means whereby filtered and unfiltered parts of liquid may be withdrawn. In the embodiment depicted in FIG. 1, first bioreactor filtration system 25, in communication with continuous liquid phase zone 18, allows for the withdrawal of intermediate permeate stream 28, which is filtered and substantially free of C1-fixing bacteria. First bioreactor retentate stream 36 allows for the return of filtered bacteria to first bioreactor 10. Liquid products withdrawn from first bioreactor 10 may therefore comprise both intermediate permeate stream 28 and intermediate bleed stream 26, which is unfiltered and contains C1-fixing bacteria (biomass) in substantially the same concentration as in the fermentation broth in continuous liquid phase zone 18 of first bioreactor 10. The relative amounts of the intermediate liquid product 32 withdrawn from first bioreactor 10 as intermediate bleed stream 26 and intermediate permeate stream 28 can be controlled to meet the objectives of maintaining a desired biomass concentration and a desired rate of product (e.g., ethanol or isopropanol) removal. In the same manner, second bioreactor filtration system 25', in communication with continuous liquid phase zone 18', allows for the withdrawal of bleed stream 40 and permeate stream 50 from a final bioreactor of bioreactor system 100, with the return of second bioreactor retentate stream 36' to continuous liquid phase zone 18' of second bioreactor 20.

Liquid culture medium may be fed, through culture medium inlet 34 to bioreactor system 100, and in particular to first bioreactor 10, to supply nutrients for maintaining bacterial growth and to replace the liquid volume lost in intermediate liquid product 32 withdrawn from first bioreactor 10, all or a portion of which may be passed to second bioreactor 20. Optionally, liquid culture medium may likewise be fed to bioreactor system 100 through separate culture medium inlet 34' to second bioreactor 20. Optionally, portions of intermediate bleed stream 26 and/or intermediate permeate stream 28 may be withdrawn from bioreactor system 100 (e.g., for process monitoring and analysis), without passing to second bioreactor 20.

Gas outlet streams 38, 38' may be withdrawn from conduits in fluid communication with respective continuous gas phase zones 22, 22', constituting bioreactor headspace volumes above continuous liquid phase zones 18, 18' comprising the culture medium and C1-fixing bacteria (i.e., comprising fermentation broth), through which the C1-containing substrate passes as a dispersed gas phase. Gas outlet streams 38, 38' may be withdrawn separately from bioreactor system 100 or, as illustrated in the embodiment of FIG. 1, combined and then withdrawn as gaseous product outlet 24. Gas outlet streams, or otherwise gaseous product outlet 24, may comprise one or more of, for example all of, (i) unreacted C1-components that passes through the fermentation broth without being metabolized (i.e., without being consumed in the biological conversion process), (ii) components of the C1-containing substrate that are substantially not involved in (i.e., substantially inert to) the biological conversion process (e.g., $N_2$), (iii) $CO_2$ produced as a metabolite of the biological conversion process, (iv) water vapor from the aqueous culture medium, and (v) various components of the C1-containing substrate that are present in minor or trace amounts (e.g., $H_2$, $H_2S$, $NH_3$, HCN).

Accordingly, FIG. 1 depicts a bioreactor system 100 in which gaseous C1-containing substrate 12 can be fed in parallel to first and second bioreactors 10, 20, whereas liquid products, which can include C1-fixing bacteria (biomass), can be fed successively from first bioreactor 10 to second bioreactor 20. In the embodiment of FIG. 1, the final bioreactor, from which bleed stream 40 and permeate stream 50 are withdrawn from bioreactor system 100, is namely second bioreactor 20. In alternative embodiments having bioreactor systems with additional bioreactors (e.g., three or four bioreactors), and specifically one or more intermediate bioreactors downstream of a first bioreactor and upstream of a final bioreactor, the gaseous and liquid feeds may be introduced to such intermediate bioreactors in a similar manner, and the gaseous and liquid products may be withdrawn from such intermediate bioreactors in a similar manner. Intermediate liquid products, including intermediate bleed and permeate streams, may be passed to and from successive intermediate bioreactors in a similar manner. In general, one or more metabolite products (e.g., ethanol) of bioreactor system 100 is recovered from bleed and permeate streams, or portions thereof, withdrawn from a final bioreactor, such as bleed stream 40 and permeate stream 50 withdrawn from second bioreactor 20 in the embodiment of FIG. 1. Optionally, such metabolite products may also be recovered from bleed and/or permeate streams, or portions thereof, withdrawn from one or more bioreactors other than a final bioreactor.

FIG. 1 therefore schematically illustrates various feed streams that are input to, and product streams that are withdrawn from, a representative bioreactor system. Embodiments of the invention can include other features not shown in FIG. 1, such as the use of (i) additives, including a basic neutralizing agent (e.g., $NH_4OH$ or NaOH) and/or an anti-foaming agent; (ii) control systems (e.g., feedback control loops) and associated equipment, instrumentation, and software, for the control of operating parameters (e.g., pH, temperature, and/or liquid level of the fermentation broth); (iii) external bioreactor recycle loops to improve interphase mass transfer; (iv) internal bioreactor structures in the continuous liquid phase zones (e.g., horizontal plates and/or packing materials) and/or in the continuous vapor phase zones (e.g., liquid distributors such as shower heads) to improve interphase mass transfer; (v) on-line sampling systems for continuous process monitoring and/or automated control; and/or (vi) recycle of liquid product(s), withdrawn from a bioreactor, to an upstream bioreactor The recovery of metabolite products such as ethanol, according to embodiments of the invention, is described in greater detail with reference to FIG. 2. As shown, all or a portion of permeate stream 50, withdrawn from bioreactor system 100 (FIG. 1) and obtained from filtration of a liquid product of this system, is partitioned into at least a first permeate portion 50' and a second permeate portion 50" that are fed to a high pressure separator 60 and a low pressure separator 70, respectively. The partitioning of the permeate stream therefore refers to dividing this stream into at least two portions, and often only two portions. "Partitioning" does not preclude the use of optional steps, before and/or after dividing the permeate stream, which steps may or may not affect the composition of the permeate stream and/or its separated portions. Such optional steps include for example (i) separating one or more additional portions (e.g., a third portion) from the permeate stream and/or its separated portions (e.g., for sampling purposes), and/or (ii) mixing the permeate stream and/or its separated portions with other streams and/or discreet additives (e.g., surfactants or neutralizing agents, such as NH$_4$OH or NaOH). In some embodiments, however, a permeate stream withdrawn from a bioreactor system may be partitioned into its separated portions that are fed to the high and low pressure separators, without any of the permeate stream or its portions undergoing (i) and/or (ii) above.

Figure 2:
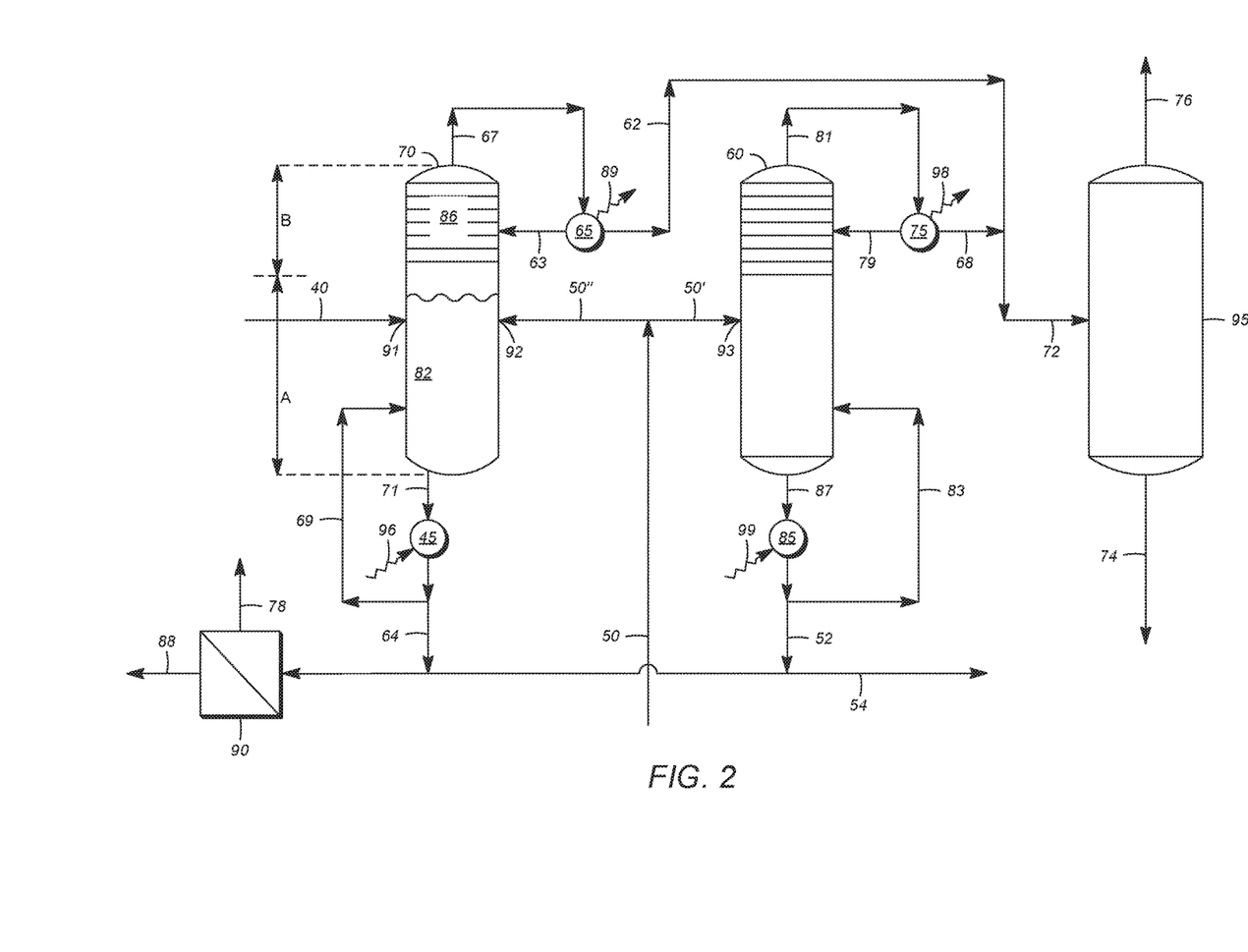
FIG. 2 depicts a process according to the illustrated, representative schematic flow diagram and associated equipment, for recovering ethanol from a bioreactor system as shown in FIG. 1, and particularly from the bleed stream and permeate stream withdrawn from this system.

Advantageously, second permeate portion 50" may be co-processed with at least a portion of bleed stream 40, also withdrawn from bioreactor system 100 (FIG. 1), to improve overall process heat integration, as described above. According to a particular embodiment, the heat integration is based on relating, or adjusting, the flow rate of second permeate portion 50" to the low pressure separator 70 at least in part based on the flow rate of bleed stream 40 to this separator. For example, an increase in the flow rate of bleed stream 40 may be accompanied by an increase in the flow rate of second permeate portion 50", with optionally the control of the flow rate of second permeate portion 50" being based on a measurement of the flow rate of bleed stream 40. Alternatively, the heat integration may account for the relatively greater contribution of the permeate stream flow rate to the combined bleed stream and permeate stream flow rates, at higher productivities of metabolite products (e.g., ethanol). For example, the relative flow rates of first permeate portion 50' to high pressure separator 60 and second permeate portion 50" to low pressure separator 70 may be based on, or adjusted according to, the total flow rate of permeate stream 50 in relation to the combined flow rate of bleed stream 40 and permeate stream 50. For example, an increase in the total flow rate of permeate stream 50 in relation to the combined flow rate of bleed stream 40 and permeate stream 50 may be accompanied by an increase in the flow rate of first permeate portion 50', relative to second permeate portion 50", with optionally the control of the first permeate portion 50' and second permeate portion 50" being based on a measurement the total flow rate of permeate stream 50 in relation to the combined flow rate of bleed stream 40 and permeate stream 50. In any of the control schemes described above, control may be performed manually or automatically, for example using a feedback control loop to adjust flow rates, i.e., partitioning, of first permeate portion 50' and/or second permeate portion 50" on the basis of one or more measured flow rates.

Unlike permeate stream 50, bleed stream 40 comprises C1-fixing bacteria (biomass), and, by virtue of the successive passage of liquid products from upstream to downstream bioreactors, at least a portion, or all, of the biomass in bleed stream 40 may be biomass originally contained in the first bioreactor (e.g., bioreactor 10 of FIG. 1). In general, bleed stream 40 may be any liquid product withdrawn from bioreactor system 100 comprising fermentation broth (e.g., as an unfiltered liquid product), including biomass, whereas permeate stream 50 may be any liquid product withdrawn from bioreactor system 100 comprising a filtered liquid product that is substantially free of biomass. Preferably, bleed stream 40 and permeate stream 50 are both liquid products obtained from a subsequent bioreactor (e.g., second bioreactor 20 of bioreactor system 100), disposed downstream of a first bioreactor, for example with respect to the liquid product flows from one bioreactor to the next. Bleed stream 40 and permeate stream 50 may be unfiltered and filtered liquid products, respectively, obtained directly from bioreactor system 100, or otherwise unfiltered and filtered products following (i) separation (e.g., other than filtration to remove biomass), for example into streams of the same or different compositions and/or (ii) mixing (e.g., with other process streams or discreet additives).

Because of the presence of biomass, separation processes performed on bleed stream 40, unlike those performed on permeate stream 50, are advantageously carried out at relatively lower temperatures to reduce fouling of separation equipment. Consequently, a maximum temperature of low pressure separator 70, to which bleed stream 40 is fed, is less than a maximum temperature of high pressure separator 60, to which permeate stream 50 is fed. According to an embodiment, a maximum temperature of a low pressure separator, to which bleed stream 40 is fed, is from about 55° C. to about 95° C., for example from about 60° C. to about 80° C. According to the same or an alternative embodiment, a maximum temperature of a high pressure separator 60 is from about 95° C. to about 125° C. or from about 100° C. to about 120° C. In general, a temperature of at least one material stream associated with high pressure separator 60 may exceed a temperature of at least one material stream associated with low pressure separator 70, such that heat may be transferred from the former to the latter. According to a particular embodiment, a minimum temperature of high pressure separator 60, for example the temperature of high pressure separator condenser 75, may exceed a maximum temperature of low pressure separator 70 for example the temperature of low pressure separator reboiler 45. Because the bleed and permeate streams 40, 50 otherwise include water and the same metabolite product(s) to be recovered, and considering the differences described above with respect to the operating temperatures of the high and low pressure separators 60, 70, the use of separations based on differences in relative volatility require relatively lower absolute pressures to perform such separations on the bleed stream, compared to the pressures used with respect to the permeate stream. According to an embodiment, low pressure separator 70 has an absolute pressure that is nearly atmospheric pressure, for example from about 50 kPa to about 150 kPa absolute pressure or from about 50 kPa to about 100 kPa absolute pressure. According to the same or an alternative embodiment, high pressure separator 60 may have an absolute pressure that is greater than that of low pressure separator, but lower than a pressure at which a final bioreactor operates. For example, high pressure separator may have a pressure from about 150 kPa to about 650 kPa absolute pressure or from about 150 kPa to about 500 kPa absolute pressure. Alternatively, low pressure separator 70 may have vacuum pressure, i.e., an absolute pressure that is below atmospheric pressure, for example from about 20 kPa to about 90 kPa absolute pressure or from about 30 kPa to about 90 kPa absolute pressure.

High and low pressure separators 60, 70 may be used to purify metabolite products (e.g., ethanol) from bleed and permeate streams 40, 50 on the basis of differences in relative volatility. In the case of the purification of ethanol, this metabolite may be relatively more volatile than water and other metabolites such as acetic acid and 2,3-butanediol, as described above. Consequently, ethanol may be enriched (i.e., present at a higher concentration) in an overhead vapor, withdrawn from high and/or low pressure separator 60, 70, compared to the ethanol concentration in permeate stream 50, fed to high pressure separator 60, and/or bleed stream 40, fed to low pressure separator 70. Likewise, ethanol may be depleted (i.e., present at a lower concentration) in the bottoms liquid, withdrawn from high and/or low pressure separator 60, 70, compared to the ethanol concentration in permeate stream 50, fed to high pressure separator 60 and/or bleed stream 40, fed to low pressure separator 70. High and low pressure separators 60, 70 include flash drums that perform a separation based on substantially a single theoretical vapor-liquid equilibrium stage. Preferably, however, high and low pressure separators 60, 70 are distillation columns that perform a separation based on multiple theoretical vapor-liquid equilibrium stages, optionally using heat input and output (e.g., reboiler heat input and condenser heat output), overhead vapor and bottoms liquid reflux, and internal structures such as perforated plates and/or packing materials. High and low pressure separators 60, 70, in addition to performing separations based on multiple vapor-liquid equilibrium stages, may, according to some embodiments, operate with the input of an upwardly flowing auxiliary gas stream (as in the case of a stripping column) or alternatively with the input of a downwardly flowing auxiliary liquid stream (as in the case of an absorber column).

According to the embodiment of FIG. 2, bleed stream 40, or at least a portion thereof, is fed, together with second permeate portion 50" to low pressure separator 70 (e.g., a low pressure, combined permeate and bleed distillation column). Low pressure separator overhead 62 is withdrawn (e.g., as a vapor fraction) and, as described above, is enriched in ethanol, relative to both bleed stream 40 and second permeate portion 50". Low pressure separator 70, is operated in a manner whereby liquid fraction 82 (i.e. combined bleed stream 40 and second permeate portion 50") is maintained in a lower section, whereas gaseous fractions, 86 that are volatilized from the liquid fraction (i.e., the liquid levels being namely liquid fractions of the bleed stream and second permeate portion, remaining after volatilization of respective gaseous fractions) can be combined in an upper section. In this manner, low pressure separator overhead 62 comprises ethanol separated from both bleed stream 40 and permeate stream 50".

According to the embodiment of FIG. 2, a low pressure separator bottoms 64 may be withdrawn from low pressure separator 70. In view of the above description, low pressure separator bottoms 64 may comprise, or consist essentially of, liquid fraction 82 of bleed stream 40 and, second permeate portion 50".

Advantageously, co-processing permeate stream 50 with at least a portion of bleed stream 40, also withdrawn from bioreactor system 100 (FIG. 1), improves overall process heat integration. According to a particular embodiment, the heat integration is based on relating, or adjusting, the flow rate of permeate stream 50 to the low pressure separator 70 at least in part based on the flow rate of bleed stream 40 to this separator. For example, an increase in the flow rate of bleed stream 40 may be accompanied by an increase in the flow rate of permeate stream 50, with optionally the control of the flow rate of permeate stream 50 being based on a measurement of the flow rate of bleed stream 40. Alternatively, the heat integration may account for the relatively greater contribution of the permeate stream flow rate to the combined bleed stream and permeate stream flow rates, at higher productivities of metabolite products (e.g., ethanol).

First permeate portion 50' may be processed in high pressure separator 60 (e.g., a high pressure permeate distillation column), to separate, or fractionate, first permeate portion 50' into at least high pressure separator bottoms 52, whereby high pressure separator overhead 68 is enriched in ethanol and high pressure separator bottoms 52 is depleted in ethanol, relative to permeate stream 50. Both high pressure separator overhead 68 and high pressure separator bottoms 52 may therefore be withdrawn from high pressure separator 60. High pressure separator bottoms 52 may be combined with low pressure separator bottoms 64, according to the embodiment of FIG. 2, as both of these streams are enriched in water, relative to permeate stream 50. Net bottoms 54 may be recycled to bioreactor system 100 (e.g., by being used in the preparation of culture medium) or sent to a wastewater treatment process. Likewise, ethanol may be depleted (i.e., present at a lower concentration) in the bottoms liquid, withdrawn from high and/or low pressure separator 60, 70, compared to the ethanol concentration in permeate stream 50, to high pressure separator 60 and/or bleed stream 40 to low pressure separator 70.

As illustrated in the embodiment of FIG. 2, both high pressure separator 60 (e.g., high pressure distillation column) and low pressure separator 70 (e.g., low pressure distillation column) generally include an overhead condenser and a bottoms reboiler These low pressure separator reboilers 45 in conjunction with a low pressure separator condenser 65, a high pressure separator condenser 75, and a high pressure separator reboiler 85, provide sites of heat consumption in such reboilers and sites of heat generation in such condensers. In view of the differences in operating temperatures between the high pressure separator 60 and low pressure separator 70, heat may be transferred between these separators, for example by using suitable heat transfer media such as cooling water or steam to provide the necessary cooling or heating duty, respectively, of the condensers and reboilers, resulting in advantageous heat integration that can reduce operating costs.

As illustrated in the embodiment of FIG. 2, one or more of the following may be possible, in view of the use of overhead condensers and bottoms reboilers: (i) low pressure separator overhead 62, in addition to low pressure separator overhead reflux portion 63, may be separated from low pressure separator vapor outlet stream 67 withdrawn from low pressure separator 70, (ii) low pressure separator bottoms 64, in addition to low pressure separator liquid reflux portion 69, may be separated from low pressure separator liquid outlet stream 71 withdrawn from low pressure separator 70, (iii) high pressure separator overhead 68, in addition to high pressure separator overhead reflux portion 79, may be separated from high pressure separator vapor outlet stream 81 withdrawn from high pressure separator 60, and (iv) high pressure separator bottoms 52, in addition to high pressure separator liquid reflux portion 83, may be separated from high pressure separator liquid outlet stream 87 withdrawn from high pressure separator 60. Further arising from the use of overhead condensers and bottoms reboilers, one or more of the following, particular flow schemes may also be possible: (i) low pressure separator vapor outlet stream 67 may be fed to low pressure separator condenser 65 to condense at least a portion thereof, return low pressure separator overhead reflux portion 63 to low pressure separator 70, and recover low pressure separator condenser heat 89, (ii) low pressure separator liquid outlet stream 71 may be fed to low pressure separator bleed reboiler 45 to vaporize at least a portion thereof, return low pressure separator bleed liquid reflux portion 69 to low pressure separator 70, and consume low pressure separator reboiler heat 96, (iii) high pressure separator vapor outlet stream 81 may be fed to high pressure separator condenser 75 to condense at least a portion thereof, return high pressure separator overhead reflux portion 79 to high pressure separator 60, and recover high pressure separator condenser heat 98, and (iv) high pressure separator liquid outlet stream 87 may be fed to high pressure separator reboiler 85 to vaporize at least a portion thereof, return high pressure separator liquid reflux portion 83 to high pressure separator 70, and consume high pressure separator reboiler heat 99.

Particularly advantageous heat integration strategies involve the transfer of heat from the high pressure separator to the low pressure separator, and especially from high pressure separator condenser 75 to a reboiler of low pressure separator 70 in the case in which the temperature of the former exceeds the temperature of latter. Accordingly, at least a portion of high pressure separator condenser heat 98 may be consumed as low pressure separator reboiler heat 96. According to the embodiment of FIG. 2, ethanol contained in both low pressure separator overhead 62 and high pressure separator overhead 68 may represent a net amount of ethanol recovered from bioreactor system 100, and consequently a net ethanol productivity of this system. As described above, bioreactor systems according to the present invention can provide advantages in terms of process heat integration, particularly in the face of relatively high permeate stream flow rates, compared to bleed stream flow rates, accompanying high ethanol productivities. Exemplary ethanol productivities are generally at least about 35 grams per day per liter of bioreactor volume (g/day/L), for example in the range from about 35 g/day/L to about 80 g/day/L, typically at least about 45 g/day/L, for example in the range from about 45 g/day/L to about 75 g/day/L, and often at least about 55 g/day/L, for example in the range from about 55 g/day/L to about 70 g/day/L. In determining the productivity rate on the basis of the bioreactor volume, this volume includes continuous liquid phase zones 18, 18' and continuous gas phase zones 22, 22' of the bioreactor(s) used in the bioreactor system.

Both low pressure separator overhead 62 and high pressure separator overhead 68, which are enriched in ethanol, may be combined into dehydration column feed stream 72. Dehydration column fractionates this stream into anhydrous ethanol product stream 76, comprising substantially pure ethanol (e.g., having a purity of at least about 99% by weight) and residual water stream 74.

According to further embodiments, low pressure separator bottoms 64 may be withdrawn from low pressure separator 70. Low pressure separator bottoms 64 may be passed to product separation system 90, which may be a product membrane filtration system, for the separation and removal of biomass fraction 78 (e.g., as a retentate fraction obtained from product separation system 90) from liquid fraction 88 (e.g., as a permeate fraction obtained from product separation system 90). The liquid fraction may be re-used in bioreactor system 100 (e.g., following one or more treatment steps to obtain water suitable for use in the system), or alternatively sent to a wastewater treatment facility. At least a portion of high pressure separator bottoms 52 and/or at least a portion of low pressure separator bottoms 64, as substantially pure water streams that optionally comprise higher-boiling metabolites such as acetic acid and 2,3-butanediol, may be recycled to bioreactor process 100, optionally following one or more treatment steps. According to the embodiment of FIG. 2, these streams 52, 64 may be combined into net bottoms 54, prior to such recycling and/or treatment. Water in streams 52, 64 may be recycled, for example, for the preparation of fresh culture medium.

In terms of biological conversion apparatuses corresponding to the embodiments depicted in FIGS. 1 and 2, it is apparent in view of the above description that such apparatuses may comprise a bioreactor system 100 comprising (i) an inlet 12 for introducing a CO-containing substrate to the bioreactor system 100, (ii) at least a first bioreactor 10 for containing a culture medium and C1-fixing bacteria to metabolize CO in the CO-containing substrate and produce ethanol, (iii) a filtration system 25' for filtering a liquid product of the bioreactor system, (iv) a bleed stream outlet 40 for withdrawing a bleed stream comprising C1-fixing bacteria, and (v) a permeate stream outlet 50 in fluid communication with a permeate side of the filtration system 25' for withdrawing a permeate stream from the bioreactor system 100, and optionally a recycle conduit 36' in fluid communication with a retentate side of the filtration system 25' for maintaining a recycle portion of C1-fioxing bacteria in the bioreactor system 100; and a low pressure separator 70 having (i) liquid volume 82 in fluid communication with both (I) the stream outlet 40, and (II) the permeate stream outlet 50, at a low pressure separator bleed stream inlet 91 and low pressure separator permeate stream inlet 92 positioned in the lower section A, and (ii) a low pressure separator bottoms outlet 64 positioned below the low pressure bleed stream inlet 91 and low pressure permeate stream inlet 92 positioned in the lower section A. The apparatus may optionally further comprise a high pressure separator 60 having (i) a first permeate portion inlet 93 in fluid communication with the permeate stream outlet 50, for receiving a first permeate portion of the permeate stream and passing a second permeate portion of the permeate stream to the low pressure separator permeate stream inlet 92, (ii) a high pressure separator overhead outlet 68, and (iii) a high pressure separator bottoms outlet 52, wherein the first permeate portion inlet 93 is positioned below the high pressure separator overhead outlet 68 and above the high pressure separator bottoms outlet 52.

Low pressure separator 70 may be configured with low pressure separator condenser 65 in fluid communication with low pressure separator vapor outlet 67 and both (i) low pressure separator overhead reflux conduit 63 and (ii) low pressure separator overhead conduit 62. Low pressure separator may also be configured with low pressure separator reboiler 45 in fluid communication with low pressure separator liquid outlet 71 and both (i) low pressure separator liquid reflux conduit 69 and (ii) low pressure separator bottoms conduit 64. High pressure separator 60 may be configured with high pressure separator condenser 75 in fluid communication with high pressure separator vapor outlet 81 and both (i) high pressure separator overhead reflux conduit 79 and (ii) high pressure separator overhead conduit 68. High pressure separator 60 may also be configured with high pressure separator reboiler 85 in fluid communication with high pressure separator liquid outlet 87 and both (i) high pressure separator liquid reflux conduit 83 and (ii) high pressure separator bottoms conduit 52. Any of, or any combination of, low pressure separator condenser 65, and low pressure separator reboiler 45, as described above, may be configured to provide heat integration with high pressure separator condenser 75 and/or high pressure separator reboiler 85, as described above. According to exemplary embodiments, high pressure separator condenser 75 may be configured (e.g., using a heat transfer medium such as cooling water or steam) to transfer heat generated in this condenser, for consumption in low pressure separator reboiler 45, as described above.

The apparatus may optionally further comprise a dehydration column 95 having (i) a dehydration column inlet 72 in fluid communication with both the low pressure separator overhead outlet 62 and the high pressure separator overhead outlet 68, (ii) a dehydration column overhead outlet 76, and (iii) a dehydration column bottoms outlet 74, wherein the dehydration column inlet 72 is positioned below the dehydration column overhead outlet 76 and above the dehydration column bottoms outlet 74.

The apparatus may optionally further comprise a product filtration system 90 in fluid communication with the low pressure separator bottoms outlet 64 for filtering a low pressure separator bottoms stream.

Overall, aspects of the disclosure are associated with biological conversion processes involving downstream recovery of ethanol from bleed and permeate streams and relate, more particularly, to performing such recovery with improved efficiency that can advantageously reduce capital (e.g., equipment) and/or operating (e.g., utility) costs. Those having skill in the art, with the knowledge gained from the present disclosure, will recognize that various changes could be made to these processes in attaining these and other advantages, without departing from the scope of the present disclosure. As such, it should be understood that the features of the disclosure are susceptible to modification, alteration, changes, or substitution without departing from the scope of this disclosure. The specific embodiments illustrated and described herein are for illustrative purposes only, and not limiting of the invention as set forth in the appended claims.

The invention claimed is:

1. A biological conversion process comprising:
  a. feeding a substrate to a bioreactor system comprising at least a first bioreactor including a culture medium and a bacterium to metabolize a carbon source in the substrate and produce at least one fermentation product;
  b. withdrawing from the bioreactor system a filtered permeate;
  c. withdrawing from the bioreactor system a bleed stream comprising bacterium;
  d. feeding at least a portion of the permeate stream to a high pressure separator;
  e. feeding at least a portion of the bleed stream to a low pressure separator.

2. The process of claim 1, further comprising, blending at least a second portion of the permeate stream with the bleed stream to provide a combined stream, and feeding at least a portion of the combined stream to the low pressure separator.

3. The process of claim 1, wherein the high pressure separator and the low pressure separator are a high pressure distillation column and a low pressure distillation column, respectively.

4. The process of claim 1, wherein the high pressure separator has an absolute pressure in the range from about 150 kPa to about 650 kPa.

5. The process of claim 1, wherein the low pressure separator has a vacuum pressure.

6. The process of claim 1, wherein the bleed stream and permeate stream are both liquid products obtained from a subsequent bioreactor, disposed downstream of the first bioreactor.

7. The process of claim 1, further comprising (i) withdrawing, from the low pressure separator, a low pressure separator overhead enriched in a fermentation product, relative to the bleed stream; and (ii) withdrawing, from the high pressure separator, a high pressure separator overhead and a high pressure separator bottoms, wherein the high pressure separator overhead is enriched in fermentation product.

8. The process of claim 7, wherein the low pressure separator overhead comprises the fermentation product separated from the bleed stream.

9. The process of claim 8, wherein the fermentation product contained in both the low pressure separator overhead and high pressure separator overhead represents a net fermentation product productivity of the bioreactor system.

10. The process of claim 9, wherein the fermentation product is ethanol, and the net ethanol productivity is at least 55 grams/day, per liter of bioreactor volume.

11. The process of claim 7, further comprising withdrawing, from the low pressure separator, a low pressure separator bottoms.

12. The process of claim 7, wherein one or more of (i) the low pressure separator overhead, in addition to a low pressure separator overhead reflux portion, are separated from a low pressure separator vapor outlet stream withdrawn from the low pressure separator, (ii) a low pressure separator bottoms, in addition to a low pressure separator boiler portion, are separated from a low pressure separator liquid outlet stream withdrawn from the low pressure separator, (iii) the high pressure separator overhead, in addition to a high pressure separator overhead reflux portion, are separated from a high pressure separator vapor outlet stream withdrawn from the high pressure separator, and (iv) the high pressure separator bottoms, in addition to a high pressure separator boilup portion, are separated from a high pressure separator liquid outlet stream withdrawn from the high pressure separator.

13. The process of claim 12, wherein one or more of (i) the low pressure separator vapor outlet stream is fed to a low pressure separator condenser to condense at least a portion thereof, return the low pressure separator overhead reflux portion to the low pressure separator, and recover low pressure separator condenser heat, (ii) the low pressure separator liquid outlet stream is fed to a low pressure separator reboiler to vaporize at least a portion thereof, return the low pressure separator liquid reflux portion to the low pressure separator, and consume low pressure separator reboiler heat, (iii) the high pressure separator vapor outlet stream is fed to a high pressure separator condenser to condense at least a portion thereof, return the high pressure separator overhead reflux portion to the high pressure separator, and recover high pressure separator condenser heat, and (iv) the high pressure separator liquid outlet stream is fed to a high pressure separator reboiler to vaporize at least a portion thereof, return the high pressure high liquid reflux portion to the high pressure separator, and consume high pressure separator reboiler heat.

14. The process of claim 13, wherein at least a portion of the high pressure separator condenser heat is consumed as low pressure separator reboiler heat.

15. The process of claim 12, wherein the low pressure separator liquid outlet stream is fed to a low pressure separator reboiler to vaporize portions thereof, return the low pressure separator liquid reflux portion to the low pressure separator, and consume low pressure separator reboiler heat.

16. The process of claim 15, wherein at least a portion of a high pressure separator condenser heat is consumed as low pressure separator reboiler heat.

17. The process of claim 11, further comprising recycling at least a portion of the high pressure separator bottoms and/or at least a portion of the low pressure separator bottoms to the bioreactor system.

18. The process of claim 1, wherein the substrate is a C1-containing substrate, the bacterium is a C1-fixing bacterium, and the at least one fermentation product is selected from the group consisting of ethanol, isopropanol and mixtures thereof.

19. The process of claim 1 additionally comprising the step of partitioning the permeate stream into at least a first permeate portion and a second permeate portion and feeding at least a portion of the first permeate stream portion to a high pressure separator and feeding the second permeate portion to a low pressure separator.

20. The process of claim 19, wherein, in the step of partitioning, a flow rate of the second permeate portion is adjusted at least in part based on a flow rate of the bleed stream.

21. The process of claim 2, further comprising (i) withdrawing, from the low pressure separator, a low pressure separator overhead enriched in a fermentation product, relative to the bleed stream; and (ii) withdrawing, from the high pressure separator, a high pressure separator overhead and a high pressure separator bottoms, wherein the high pressure separator overhead is enriched in fermentation product.

22. The process of claim 21, wherein the low pressure separator overhead comprises fermentation product separated from both the second portion of the permeate stream and the bleed stream.

23. The process of claim 22, wherein fermentation product contained in both the low pressure separator overhead and high pressure separator overhead represents a net fermentation product productivity of the bioreactor system.

24. The process of claim 23, wherein the fermentation product is ethanol, and the net ethanol productivity is at least 55 grams/day, per liter of bioreactor volume.

\* \* \* \* \*